US005835214A

United States Patent [19]
Cabib et al.

[11] Patent Number: 5,835,214
[45] Date of Patent: Nov. 10, 1998

[54] METHOD AND APPARATUS FOR SPECTRAL ANALYSIS OF IMAGES

[75] Inventors: Dario Cabib, Timrat; Zvi Friedman, Kiryat Bialik; Stephen G. Lipson, Haifa; Robert A. Buckwald, Ramat Ishay, all of Israel

[73] Assignee: Applied Spectral Imaging Ltd., Migdal Haemek, Israel

[21] Appl. No.: 831,380

[22] Filed: Apr. 1, 1997

Related U.S. Application Data

[63] Continuation of Ser. No. 635,820, Apr. 22, 1996, which is a continuation of Ser. No. 575,191, Dec. 20, 1995, which is a continuation-in-part of Ser. No. 571,047, Dec. 12, 1995, Pat. No. 5,784,162, which is a continuation-in-part of Ser. No. 392,019, Feb. 21, 1995, Pat. No. 5,539,517, which is a continuation-in-part of Ser. No. 107,673, Aug. 18, 1993, abandoned.

[30] Foreign Application Priority Data

Feb. 22, 1991 [IL] Israel ............................................ 97328

[51] Int. Cl.⁶ .................................................. G01C 9/02
[52] U.S. Cl. ........................................ 356/346; 356/352
[58] Field of Search ...................... 356/346; 250/339.07, 250/339.08; 382/128

[56] References Cited

U.S. PATENT DOCUMENTS

| | | |
|---|---|---|
| 3,702,735 | 11/1972 | Potter, Jr. . |
| 4,509,857 | 4/1985 | Vermande . |
| 4,976,542 | 12/1990 | Smith ...................................... 356/346 |
| 5,377,003 | 12/1994 | Lewis et al. ............................ 356/346 |
| 5,528,368 | 6/1996 | Lewis et al. ............................ 356/346 |

FOREIGN PATENT DOCUMENTS

| | | |
|---|---|---|
| 47-41887 | 12/1972 | Japan . |
| 61-88116 | 8/1985 | Japan . |
| 64-6529 | 6/1987 | Japan . |
| 64-280925 | 10/1989 | Japan . |
| 2-339547 | 11/1990 | Japan . |
| 90/07698 | 7/1990 | WIPO . |
| 94/19667 | 9/1994 | WIPO . |

OTHER PUBLICATIONS

Hammer et al, "Remote Sensing of Earth's Atmosphere and Surface Using a Digital Array Scanned Interferometer", *J. Imaging Science & Tech.*, vol. 35, No. 5 pp. 417–422 (1992).

Coarer et al., "Un Spectrometre Imageur Pour L'astronomie", *Comptes Rendus de l'Academie des Sciences*, No. Series II, pp. 45–49 (1992).

Roesler, et al., "Fabry–Perot/CCD Observations of [S III] and [S II] Emissions from the Jupiter Plasma Torus", *Astrophysical Journal*, 259:900–907 (1982).

*Primary Examiner*—Samuel A. Turner
*Attorney, Agent, or Firm*—Mark M. Friedman

[57] ABSTRACT

A method and apparatus for analyzing an optical image of a scene to determine the spectral intensity of each pixel thereof, by: collecting incident light from the scene; scanning the incident light; passing the scanned light through an interferometer which outputs modulated light corresponding to a predetermined set of linear combinations of the spectral intensity of the light emitted from each pixel; focusing the light outputted from the interferometer on a detector array; and processing the output of the detector array to determine the spectral intensity of each pixel thereof.

34 Claims, 6 Drawing Sheets

METHOD AND APPARATUS FOR SPECTRAL ANALYSIS OF IMAGES

This is a continuation in part of U.S. patent application Ser. No. 08/635,820 filed Apr. 22, 1996 pending, which is a continuation of U.S. patent application Ser. No. 08/575,191 filed Dec. 20, 1995 pending, which is a continuation in part of U.S. patent application Ser. No. 08/571,047 filed Dec. 12, 1995 now U.S. Pat. No. 5,784,162, which is a continuation in part of U.S. patent application Ser. No. 08/392,019 filed Feb. 21, 1995, now U.S. Pat. No. 5,539,517 issued Jul. 23, 1996, which is a continuation in part of U.S. patent application Ser. No. 08/107,673 filed Aug. 18, 1993, now abandoned.

The present invention relates to a method and apparatus for spectral analysis of images, and particularly for analyzing an optical image of a scene to determine the spectral intensity of each pixel thereof.

A spectrometer is an apparatus designed to accept light, to separate (disperse) it into its component wavelengths, and detect the spectrum. An imaging spectrometer is one which collects incident light from a scene and analyzes it to determine the spectral intensity of each pixel thereof.

The conventional image spectrometer includes a slit in the image plane for scanning the scene to be analyzed and focusing the scanned light on an array of detectors. If a two-dimensional detector array is used, one of the dimensions of the array is used to sample the different wavelengths of a single pixel; the field of view is covered by a one-dimensional scanner, and the other dimension of the array. If a one-dimensional detector array is used, the field of view is scanned mechanically in two directions, and all the detectors are used at any given time only to sample the different wavelengths of one pixel. In both cases, the slit in the image plane ensures that each detector sees only the contribution of one pixel at a single wavelength at any time; otherwise, it would be impossible to separate the spectra of each pixel.

However, the conventional slit-type imaging spectrometer suffer from the disadvantage that most of the pixels of one frame are not measured at any given time, even though the fore optics of the spectrometer actually collects incident light from all of them simultaneously. Thus, the conventional slit-type technique is wasteful of the available information since, except for one wavelength, the technique rejects most of the radiation emitted by the measured pixel at any given time and reaching a particular detector. The result is that either a relatively large frame time is required to obtain the necessary information, or the signal-to-noise ratio (sensitivity) is substantially reduced.

An object of the present invention is to provide a novel method and apparatus for spectral analysis of images which have advantages in the above respects.

More particularly, an object of the invention is to provide a method and apparatus for spectral analysis of images which better utilizes all the information available from the collected incident light of the image to substantially decrease the required frame time and/or to substantially increase the signal-to-noise ratio, as compared to the conventional "slit" type of imaging spectrometer.

According to the present invention, there is provided a method of analyzing an optical image of a scene to determine the spectral intensity of each pixel thereof, comprising: collecting incident light from the scene; scanning the incident light along at least one dimension; passing the scanned light through an interferometer which outputs modulated light corresponding to a predetermined set of linear combinations of the spectral intensity of the light emitted from each pixel; focusing the light outputted from the interferometer on a detector array; and processing the output of the detector array to determine the spectral intensity of each pixel thereof.

According to the present invention there is provided a method for simultaneously measuring the spectral intensity as a function of wavelength of all the pixels of a two-dimensional scene while detecting a real and stationary image of the scene, the method comprising the steps of: (a) collecting incident light simultaneously from all points of the two-dimensional scene using collimating optics; (b) passing said incident collimated light through an interferometer system having a number of elements, so that said light is first split into two coherent beams which travel along different optical paths inside said interferometer and then said two coherent beams recombine to interfere with each other to form an exiting light; (c) passing said exiting light through a focusing optical system which focuses said exiting light on a detector having a two dimensional array of detector elements, so that at each instant each of said detector elements is the image of one and always the same pixel of said scene for the entire duration of the measurement, so that the real image of the scene is stationary on the plane of the detector array at any time during the measurement the image is still visible and recognizable, and so that each of said detector elements produces a signal which is a particular linear combination of light intensity emitted by said pixel at different wavelengths, wherein said linear combination is a function of instantaneous optical path difference; (d) translating at least one of said elements of said interferometer system, so that said optical path difference between said two coherent beams generated by said interferometer system is scanned simultaneously for all the pixels of the scene; and (e) recording said signals of each of said detector elements as functions of time using a recording device.

According to the present invention there is provided a method for simultaneously measuring the spectral intensity as, a function of wavelength of all the pixels of a two-dimensional scene located at infinity while detecting a real and stationary image of the scene, the method comprising the steps of: (a) collecting naturally collimated incident light simultaneously from all points of the two-dimensional scene; (b) passing said incident naturally collimated light through an interferometer system having a number of elements, so that said light is first split into two coherent beams which travel along different optical paths inside said interferometer and then said two coherent beams recombine to interfere with each other to form an exiting light; (c) passing said exiting light through a focusing optical system which focuses said exiting light on a detector having a two dimensional array of detector elements, so that at each instant each of said detector elements is the image of one and always the same pixel of said scene for the entire duration of the measurement, so that the real image of the scene is stationary on the plane of the detector array at any time during the measurement the image is still visible and recognizable, and so that each of said detector elements produces a signal which is a particular linear combination of light intensity emitted by said pixel at different wavelengths, wherein said linear combination is a function of instantaneous optical path difference; (d) translating at least one of said elements of said interferometer system, so that said optical path difference between said two coherent beams generated by said interferometer system is scanned simultaneously for all the pixels of the scene; and (e) recording said signals of each of said detector elements as functions of time using a recording device.

According to the present invention there is provided a spectroscopic imaging device for simultaneously measuring the spectral intensity as a function of wavelength of all the pixels of a two-dimensional scene while detecting a real and stationary image of the scene, the device comprising: (a) collimation means for directing light from the pixels of the scene at an interferometer, said interferometer being of the type which has at least one moveable mirror which can be positioned to produce a multiplexed spectral output of said light passing through said interferometer at a plurality of select positions of said moveable mirror; (b) means operatively connected to the interferometer for positioning said moveable mirror of said interferometer, wherein said interferometer maintains the image fidelity of the scene as said light passes through said interferometer; and (c) means for collimating and directing said light passing through said interferometer at a focal plane array detector comprising a two-dimensional array of charge coupled devices, wherein said charge coupled devices of said focal plane array detector measures the intensity of said light from each of the pixels of the scene at each of said plurality of select positions of said moveable mirror.

The method may be practiced by utilizing various types of interferometers, both of the moving type wherein the OPD (optical path difference) is varied to modulate the light by moving an element in the interferometer, and of the non-moving type wherein the OPD is varied with the angle of incidence of the incoming radiation. Thus, in the moving type interferometer, at each instant each detector sees the same linear combination of the spectral content of the scene even though each detector looks at a different point of the scene; when the scanner completes scanning one frame, the complete frame will have been scanned at all relevant linear combinations of the spectral content. In the non-moving type interferometer, wherein the OPD varies with the angle of incidence of the incoming light, at each instant each detector sees a different point of the scene at a different linear combination of the spectral content; when the scanner completes scanning one frame, the complete frame will have been scanned at all relevant linear combinations of the spectral content.

For purposes of illustration, the invention is described below as implemented by use of the Fabry-Perot and Michelson interferometers as examples of the moving-type interferometers, and as implemented by use of the Michelson and Sagnac interferometers as examples of the non-moving type interferometers.

The invention also provides apparatus for spectral analysis of images in accordance with the above method.

The methods and apparatus in accordance with the above features differ from the conventional slit-type imaging spectrometer by utilizing an interferometer as described above, instead of a grating or a prism, without is limiting the collected energy with an aperture or slit, thereby substantially increasing the total throughput of the system. Such methods and apparatus thus better utilize all the information available from the incident light of the scene to be analyzed, thereby substantially decreasing the measuring time and/or substantially increasing the signal-to-noise ratio (sensitivity).

Consider, for example, the "whisk broom" design described in John B. Wellman, Imaging Spectrometers for Terrestrial and Planetary Remote Sensing, SPIE Proceedings, Vol. 750, p. 140 (1987).

Let n be the number of detectors in the linear array, m×m the number of pixels in a frame and T the frame time.

The total time spent on each pixel in one frame summed over all the detectors of the array is:

$$\frac{nT}{m^2}$$

By using the same size array and the same frame rate in a method according to the present invention, the total time spent summed over all the detectors on a particular pixel is the same, $nT/m^2$. However, whereas in the conventional grating or prism method the energy seen by every detector at any time is of the order of $1/n$ of the total because the wavelength resolution is $1/n$ of the range, in a method according to the present invention the energy is of the is order of unity because the modulating function is a sinusoidal (Michelson) or similar periodic function (low finesse Airy function with Fabry-Perot) whose average over many periods is 50%. This results in an improved signal to noise ratio, of the order of $n/2$. For a mathematical treatment and definition of the Fabry-Perot interferometer and a definition of the Airy Function, see Max Born and Emil Wolf, Principles of Optics, Pergamon Press, 1980, p. 329.

In all the embodiments of the invention described below, all the required optical phase differences are scanned simultaneously with the spatial scanning of the field of view in order to obtain all the information required to reconstruct the spectrum, so that the spectral information is collected simultaneously with the imaging information.

The invention can be used with many different optical configurations, such as a telescope for remote sensing, a microscope for laboratory analysis, fiber optics for industrial monitoring, and others. In addition, any wavelength range can be selected with appropriate filters and optics.

Further features and advantages of the invention will be apparent from the description below.

The invention is herein described, by way of example only, with reference to the accompanying drawings, wherein.

Figure 1:
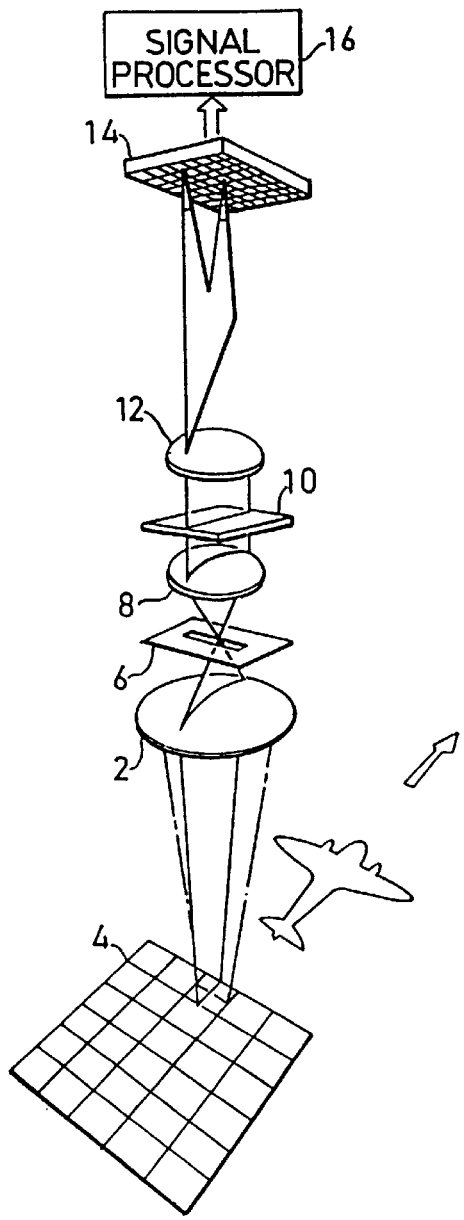
FIG. 1 illustrates a conventional (prior art) slit-type imaging spectrometer.

For purposes of better understanding the present invention, as illustrated in FIGS. 2–7 of the drawings, reference is first made to the construction and operation of a conventional (i.e., prior art) slit-type imaging spectrometer utilizing a two-dimensional array of detectors as illustrated in FIG. 1.

Thus, the prior art slit-type imaging spectrometer as illustrated in FIG. 1 comprises a collection optical system, such as a telescope as indicated at 2, for collecting the incident light from the scene, schematically indicated at 4 and outputting substantially parallel light onto a first focal plane occupied by a slit 6 to define the field of view. The light exiting from slit 6 is collimated in a collimator lens 8 and is passed through a transmission grating 10 to separate the various wavelengths. The output from grating 10 is focused by a focusing lens 12 onto a two-dimensional detector array 14 in a second focal plane. The output of detector array 14 is fed to a signal processor 16.

In the two-dimensional array of detectors 14 illustrated in the prior art imaging spectrometer of FIG. 1, the movement of the system (e.g., when embodied in an aircraft) effects the scanning along one dimension. The scanning along the second dimension is effected by the slit 6 which is oriented perpendicularly to the direction of movement of the system. The slit 6 thus assures that each detector within the array 14 sees only the contribution of one pixel at a single wavelength at any time; this is necessary to separate the spectra of each pixel.

As described earlier, the disadvantage of this prior art method illustrated in FIG. 1 is that most of the pixels of one frame are not measured at any given time even though the telescope (2 or other collecting optics) actually collects energy from all of them simultaneously. As a result, the required frame time is significantly increased, and/or the signal-to-noise ratio (sensitivity) is substantially decreased.

Figure 2:
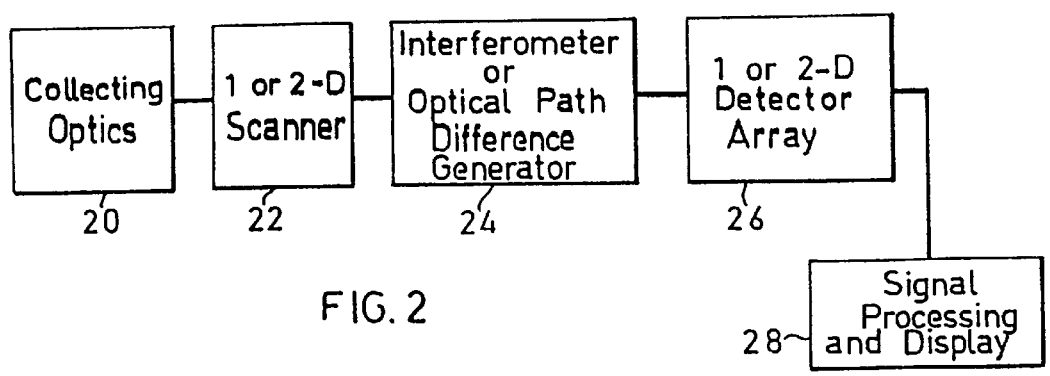
FIG. 2 is a block diagram illustrating the main components of an imaging spectrometer constructed in accordance with the present invention.

FIG. 2 is a block diagram illustrating the main components of an imaging spectrometer constructed in accordance with the present invention.

Thus, the imaging spectrometer of FIG. 2 includes: a collection optical system, generally designated 20; a one-dimensional or two-dimensional scanner, as indicated by blocks 22; an optical path difference (OPD) generator or interferometer, as indicated by block 24; a one-dimensional or two-dimensional detector array, as indicated by block 26; and a signal processor and display, as indicated by block 28.

A critical element in the novel system is the optical path difference generator or interferometer 24, which outputs modulated light corresponding to a predetermined set of linear combinations of the spectral intensity of the light emitted from each pixel of the scene to be analyzed. The output of the interferometer is focused onto the detector array 26. Thus, all the required optical phase differences are scanned simultaneously with the spatial scanning of the field of view in order to obtain all the information required to reconstruct the spectrum. The spectral information is thus collected simultaneously with the imaging information, thereby permitting analysis of the image in a real-time manner.

Figure 3:
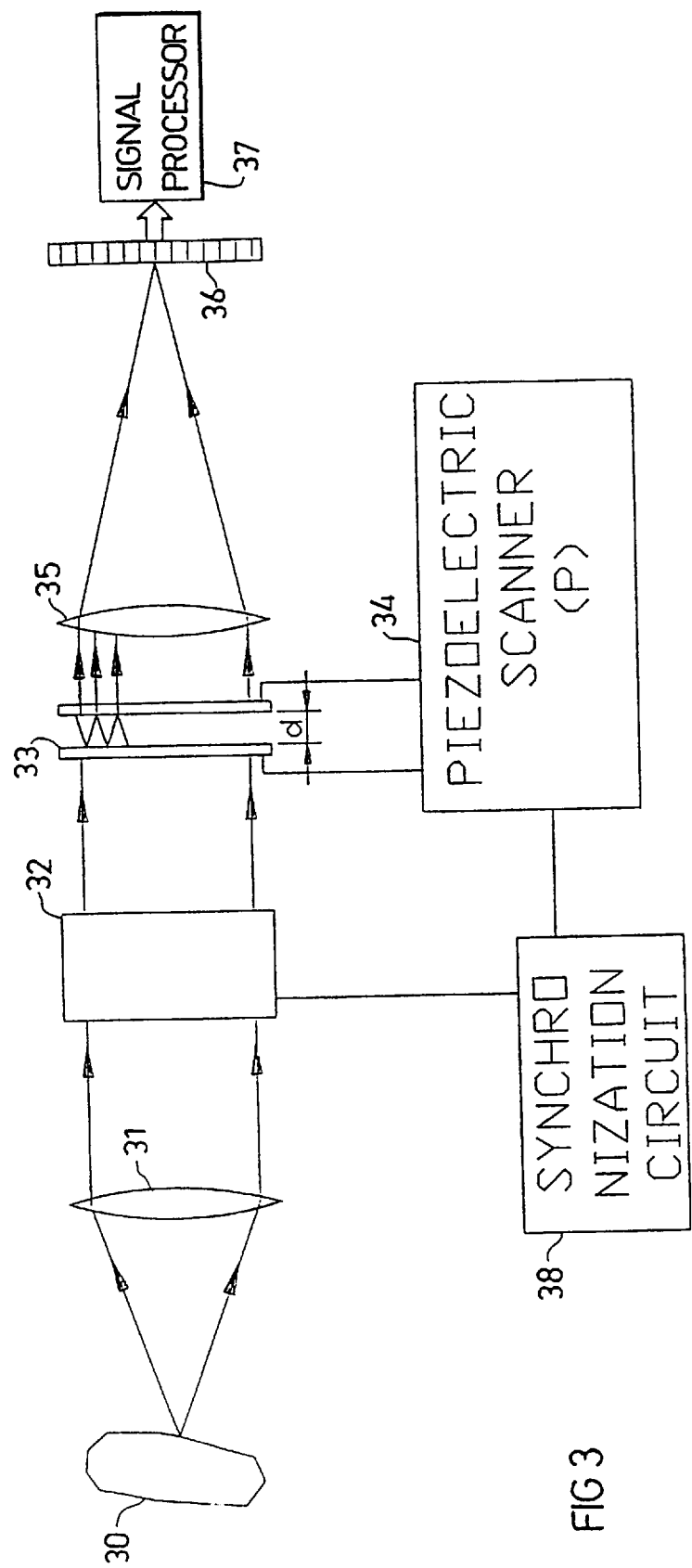
FIG. 3 is a diagram illustrating an imaging spectrometer constructed in accordance with the present invention based on the use of a moving-type interferometer, namely a Fabry-Perot interferometer with scanned thickness.

FIG. 3 illustrates one form of imaging spectrometer constructed in accordance with the present invention. This spectrometer is based on the use of a moving type interferometer in which the OPD is varied to modulate the light, namely a Fabry-Perot interferometer 33 with scanned thickness.

Thus, the imaging spectrometer illustrated in FIG. 3 comprises a source or scene, generally designated 30, to be analyzed to determine the spectral intensity of each pixel of the scene. The scene 30 may be a source of incoherent non-monochromatic radiation. It may be at a distance for remote-sensing applications, in which case the collection optical system, schematically indicated as 31, would be a telescope; alternatively, the scene 30 may be close for microscopic analysis, in which case the collection optical system 31 would be a microscope.

Optical system 31 provides an output to a two-dimensional mechanical scanner, e.g., a mirror scanner as indicated at 32, to scan the scene. The output from scanner 32 is fed to a Fabry-Perot interferometer 33 having an etalon made of two plane, parallel reflectors spaced at a distance "d" from each other. In this example, the spacing distance "d" is variable by using a mechanical scanner, in this case a piezo-electric scanner 34.

The output from the Fabry-Perot interferometer 33 is fed through a refocusing optical system 35 onto a two-dimensional array of detectors 36 whose outputs are fed to a signal processor 37.

Optical system 31, e.g., an afocal telescope or microscope, produces a substantially parallel beam (i.e., exactly parallel or having a very large F/No) at its output, because in this way every detector within the array 36 corresponds to a single optical phase difference through the etalon 33 of the Fabry-Perot interferometer 33. The optical system 31 can be either refractive or reflective. The etalon 33 of the interferometer is at 90° to the optical axis of the system. It will be noted that no use is made of a field-of-view limiting aperture or slit.

The imaging spectrometer illustrated in FIG. 3 operates as follows:

A detector element i of the array 36 receives radiation from a beam which traverses the etalon 33 at a fixed angle ($\phi_i$) between its line of sight and the normal to the etalon, and therefore it sees this radiation always through an optical phase difference $\delta_i$, given by $$\delta_i = \frac{2\pi 2d \sqrt{n^2 - \sin^2\phi_i}}{\lambda} \tag{1}$$

where $\lambda$ is the wavelength of the radiation considered, and n is the index of refraction of the air between the plates.

The total radiation reaching detector $i_k$ at any given time from a specific pixel k of the radiation input 30 of that pixel's spectrum with the Airy function, as follows (Max Born and Emil Wolf, Principles of Optics, Pergamon Press, 1980, page 327):

$$I_{i_k} = \int_{\lambda_1}^{\lambda_2} \frac{I_k(\lambda)}{1 + F\sin\left[\frac{1}{2}\delta_i(\lambda)\right]} d\lambda \tag{2}$$

where
$\lambda_1, \lambda_2$ = limits of the spectral range
$I_k(\lambda)$ = spectral intensity of the source at pixel k
F = coefficient of finesse, is related to the reflectivity of the etalon R, by:

$$F = \frac{4R}{(1-R)^2}$$

$i_k$ = that particular detector which images pixel k through an optical phase difference $\delta_i(\lambda)$ Following is one of many ways of scanning the field of view and the thickness of the etalon 33.

Suppose the array 36 is composed of a linear set of N detectors, whose signals can be monitored simultaneously and independently. Suppose M performs a raster type scan of m lines (larger than N) and that the plane of the paper in FIG. 3 is the vertical direction. Every time M has scanned one horizontal line, the thickness "d" of the etalon 33 is incremented by the piezo-electric scanner 37 one step in synchronization with the vertical scanner 32 starting from d=0, until N lines are scanned, and N thickness steps are made. At this moment the etalon thickness is returned to the original value, and the thickness scanned again. The process is repeated until the scanner has scanned one complete frame.

Except for a marginal region of N pixels at the top and at the bottom of the field of view, all the pixels of the field of view are measured with N optical phase differences by different detectors. All the detector signals are sampled and recorded at a high rate, such that all the needed information is collected and fed to the signal processor 37 to reconstruct both the image and the spectra of all the pixels.

Another possible configuration is one which includes a two-dimensional array of detectors: in this case the same idea applies, but one spatial scan is saved.

For example, if the array is an N×m matrix in a "push broom" approach similar to that described on Page 142 of John B. Wellman, Imaging Spectrometers for Terrestrial and Planetary Remote Sensing, SPIE Proceedings, Vol. 750, p. 140 (1987), the N lines and m columns correspond to the same matrix in object space.

In this configuration, the Fabry-Perot thickness or optical phase difference is kept fixed for the time of integration of one line. Then the scanner performs a step vertically, and the Fabry-Perot thickness d is stepped in synchronization by one step, starting from zero, until N steps are performed. At this point the scanner continues scanning vertically, the thickness starts from zero again, and the steps are repeated until the complete field of view is scanned.

In this way all the pixels are measured through all the optical phase differences, and the recorded information is processed to yield the spectra of every pixel.

It should be noted that the readout architecture of the array must be the same as that of page 142 of the above-cited John B. Wellman publication for "push broom": the charge pattern of N lines of the scene from one Fabry-Perot thickness is integrated in the array simultaneously during the time of one line of a video frame. This charge pattern is read out while integrating the next Fabry-Perot thickness.

The reconstruction of the spectrum of every pixel may be done by suitable mathematical processing, as follows:

We divide the spectral range of interest $\lambda_1$ to $\lambda_2$, into N intervals. If we approximate the integral of Eq. (2) as a sum over N wavelength intervals, Eq. (2) is the product of an N×N dimensional matrix given by:

$$A_{ij} = \frac{1}{1 + F\sin\frac{2\delta_{ij}}{2}} \quad (3)$$

and an N dimensional vector $I_k(\lambda_j)$, where j scans the N wavelength intervals, and k is a specific pixel in the field of view. If we invert the matrix $A_{ij}$ and multiply it by the vector $I_{ik}$ ($i_k=1, \ldots$ to n), we obtain the vector $I_k(\lambda_j)$ which is the spectrum of pixel k.

With respect to spectral resolution, consider two quasi monochromatic sources placed at the same pixel.

Preferably, the finesse F of the Fabry-Perot interferometer 33 is in the region around F=10, because (from FIG. 7.58 of the above-cited Born and Wolf publication) we see that in this case there is enough modulation in the Airy function, and that at the same time it does not yield very narrow lines; in fact this configuration does not correspond to a very high wavelength resolution but it is necessary in order not to lose a significant amount of radiation between the narrow peaks of the Airy function. This is a desirable situation, since in any case, because of the imaging, a high resolution may yield too much information to handle.

The treatment of the resolution on Page 334 of the Born and Wolf publication still holds, because if we set $$\sin\frac{\epsilon}{4} = \frac{\epsilon}{4} = \frac{1}{\sqrt{F}} = \frac{1}{0.3} \sim 0.3 \quad (4)$$

we see that we make an error of about 10% in approximating $\sin \epsilon/4$ with $\epsilon/4$.

So we have in this case $$\mathcal{F} = \frac{\pi}{2}\sqrt{F} = 5 \quad (5)$$

and the resolving power is $$\lambda/\Delta\lambda \sim 2\mathcal{F}nd/\lambda \quad (6)$$

In order to get an idea of the order of magnitude, and check consistency, let us assume $$N=50 \text{ detectors in the array} \quad (7)$$

$$\Delta\lambda = \frac{3\mu}{50} = 0.06\mu \quad (8)$$

and $$\lambda = 2 \text{ to } 5\,\mu. \quad (9)$$

Therefore d is the range $$d = \frac{\lambda^2}{\Delta\lambda}(2\mathcal{F}n)^{-1} \quad (10)$$

Taking n=1 for air, (10) gives $$d = \frac{10}{0.06 \cdot 10} = 16\mu. \quad (11)$$

The range of d is such that it scans the same range of optical phase differences as the wavelength range; therefore, $$\frac{d_2}{\lambda_1} - \frac{d_1}{\lambda_1} = \frac{d}{\lambda_1} - \frac{d}{\lambda_2} \quad (12)$$

or $$d_2 - d_1 = d\left[1 - \frac{\lambda_1}{\lambda_2}\right] = 16 \cdot 0.3 = 5\mu \quad (13)$$

Therefore the thickness steps are of the order of $$\frac{5\mu}{50} = 0.1\mu \quad (14)$$

In the 8 to 14 $\mu$ spectral range we have $$\Delta\lambda = \frac{6}{50} = 0.12\mu, \quad (15)$$

$$d = \frac{11^2}{0.12 \cdot 10} = 100\mu \quad (16)$$

and $$d_2 - d_1 = 100\left(1 - \frac{8}{14}\right) = 43\mu \quad (17)$$

Therefore, the steps of thickness are of the order of 1 $\mu$. In the visible range 0.4 to 0.8 $\mu$, $\Delta\lambda=0.008$ $\mu$, and therefore, $$d = \frac{0.6^2}{0.008 \cdot 10} = 4.5\mu. \quad (18)$$

From (18)

$$d_2 - d_1 = 4.5\left(1 - \frac{1}{2}\right) = 2.25\mu \quad (19)$$

and therefore the steps in d are $$\frac{2}{50} = 0.04\mu. \qquad (20)$$

In summary, the significant features in the system illustrated in FIG. 3 include: i) the special matching of the interferometer thickness range and finesse, with the detector array size and number of detectors and the spectral resolution; and ii) the synchronization between the thickness scanning and the spatial scanning, to obtain the spectral and the spatial information simultaneously in the time one frame is built.

It will be seen when using the moving type interferometer as illustrated in FIG. 3, a beam entering the interferometer at a small angle ($\phi$=0) to the optical axis undergoes an optical path difference which varies as $\phi^2$ or higher power of $\phi$. All the spectral information in all the pixels may be collected by scanning the optical path difference in synchronization with it. At the end of one frame, every pixel has been measured through all the optical path differences by different detectors. By careful bookkeeping and by applying the appropriate matrix inversion (like Fourier transformation), the spectrum of every pixel may be calculated. The bookkeeping is needed because different detectors gather the information of different OPDs of one pixel at different times. Thus, in the time of 30 msec (the usual frame time of a standard video), a spectrum may be measured for every pixel of a standard video frame. This is of the order of 100 resolution points per pixel, with a typical matrix of 500×500 pixels per frame.

THE CONSTRUCTION OF FIG. 4

Figure 4:
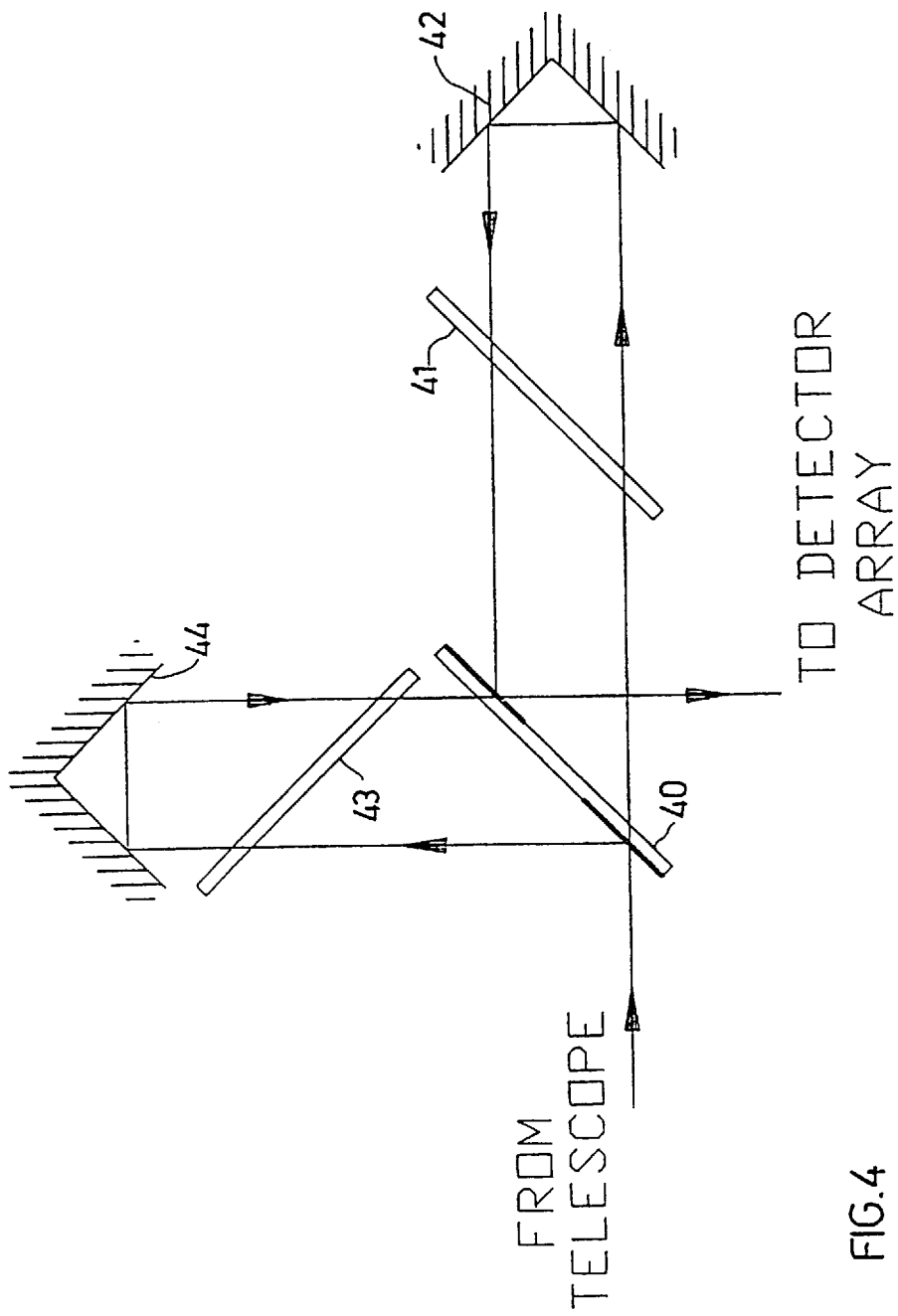
FIG. 4 illustrates a Michelson interferometer with retroreflectors used as a non-moving type interferometer in the imaging spectrometer of FIG. 2.

Instead of using a moving-type interferometer wherein the OPD (optical path difference) varies by moving an element in the interferometer (namely changing the spacing d between the plate mirrors in the Fabry-Perot interferometer illustrated in FIG. 3), the invention may also be implemented by using a non-moving type interferometer, in which case the OPD varies with the angle of incidence of the incoming radiation. FIG. 4 illustrates the invention implemented by using the latter type interferometer, namely by using a Michelson type interferometer.

Thus, the interferometer illustrated in FIG. 4 includes a beam splitter 40 receiving the beam from the optical collection system and scanner (31 and 32, respectively, FIG. 3), and splitting the beam into two paths. One path includes a compensator 41 and a retroreflector 42; and the second path includes a compensator 43 and a retroreflector 44. The two compensators, 41, 43 are identical blocks of the same material and of the same thickness, and are positioned antisymmetrically in the two arms so that only beams that are parallel to the optical axis are compensated. The two retroreflectors, 42, 44 are positioned at equal distances from the beam splitter 40. The beam splitter 40 has a half reflecting coating only on a portion of its surface on each side so that the translation of the beam through the corner cube is exploited to obtain a completely compensated system for rays parallel to the optical axis.

Thus, in the Michelson type interferometer as illustrated in FIG. 4, the beam that is parallel to the optical axis of the system is compensated between the two arms of the interferometer, whereas the beams in directions that are off the optical axis of the system undergo OPDs (optical path differences) between the two arms which vary linearly with the incident angle. The differences are proportional to the angular deviation from the optical axis.

Therefore, when the collimated beams at the exit of the interferometer are focused on a detector array, such as array 36 in FIG. 3, each element of the array will receive light that underwent different OPDs between the two arms.

Thus, with compensator 41 parallel to the beam splitter 40, and compensator 42 perpendicular to it, the optical path difference between the two arms can be shown to satisfy, for small $\phi$'s, the following relation:

$$OPD(\phi) = 2d\sin\phi_0 \left[ 1 - \frac{\cos\phi_0}{\sqrt{n^2 - \sin^2\phi_0}} \right] \phi \qquad (21)$$

with $\phi_0$=angle between the beam splitter 40 and the optical axis. For simplicity $\phi_0$ can be taken as 45°, but this is not necessary. n is the index of refraction of the two compensators, 41, 43; d is the compensator thickness; and $\phi$ is the angular deviation from the optical axis.

For example, if the required change in OPD between two adjacent detectors is ≈1 $\mu$, and the change in directions between the fields of view of two neighboring detectors is ≈1 mrad, d turns out to be of the order of 1 mm. In fact $$d = \frac{1\mu}{\frac{2\sqrt{2}}{2}\left[1 - \frac{\frac{\sqrt{2}}{2}}{\sqrt{4-\frac{1}{2}}}\right] \cdot 10^{-3}} \approx 1mm \qquad (22)$$

Note that if compensator 41 is removed and beam splitter 40 is half reflecting on the whole surface on the side of the incoming beam, then we obtain another viable configuration with a compensated optical axis.

With respect to the spectral resolution of the FIG. 4 configuration, assume that the spectral range is limited to $$\lambda_1 \leq \lambda \leq \lambda_2$$

by using a suitable filter.

Because of the Nyquist theorem, at least two samples must be measured. Since one period is an OPD change of one wavelength, the minimum difference in OPD seen by two adjacent detector elements must be $$\lambda_1/2.$$

Since the period increases with $\lambda_1$, it is obvious that this corresponds to more than two samples per period for all the other wavelengths.

Assume now that the incident radiation consists of two lines at wave numbers v and v+$\Delta$v with an intensity of $I_0$. The resultant intensity for an OPD of x is:

$$I(x)=0.5I_0(1+2\cos 2\pi vx)+0.5I_0(1+2\cos 2\pi(v+\Delta v)x) \qquad (23)$$

If we subtract the constant term, we obtain, $$\begin{aligned}\hat{I}(x) &= I(xd) - I_0 \\ &= I_0[\cos(2\pi vx) + \cos\pi(v+\Delta v)x] \\ &= 2I_0\left[2\pi\left(v+\frac{\Delta v}{2}\right)x\right]\cos\pi\Delta vx\end{aligned} \qquad (24)$$

Similar to the Rayleigh criterion, we define the two line "resolved" if the ratio, $$\frac{\hat{I}(x)}{I(0)}$$

is lower than a predetermined amount, say 0.9. This gives a condition for the maximum value of x, $x_{max}$, needed to get the defined resolution.

The value of $x_{max}$ which satisfies the above condition is:

$$\cos \pi \Delta v x_{max} \leq 0.9 \quad (25)$$

or $$x_{max} \geq \frac{0.143}{\Delta v} \quad (26)$$

Now let $N_d$ be the total number of the detectors in the array. Then:

$$x_{max} \geq N_d \frac{\lambda_1}{2} \quad (27)$$

and $$N_d \frac{\lambda_1}{2} = \frac{0.143}{\Delta v} \quad (28)$$

or $$\Delta v = \frac{0.286}{\lambda_1 N_d} \quad (29)$$

For $v_2 = 1/\lambda_2$ $$\frac{\Delta v}{v_2} = \Delta v \lambda_2 = \frac{0.286}{N_d} \cdot \frac{\lambda_1}{\lambda_2}$$

As a numerical example:
if $\lambda_1 = 2 \,\mu m$, $\lambda_2 = 5 \,\mu m$ and $N_d = 100$ $$\frac{\Delta v}{v_2} = 0.7\%$$

In summary, the uniqueness of the system illustrated in FIG. 4 is represented by: i) the OPD is a linear function of the angle of incidence of the incoming radiation on the interferometer, so that different detectors of the array see it at different OPDs. This fact, combined with the spatial scanning and proper bookkeeping, allows the spectrum to be built by inverse transformation simultaneously with the picture, similarly to the Fabry-Perot case described above.

THE CONSTRUCTION OF FIG. 5

Figure 5:
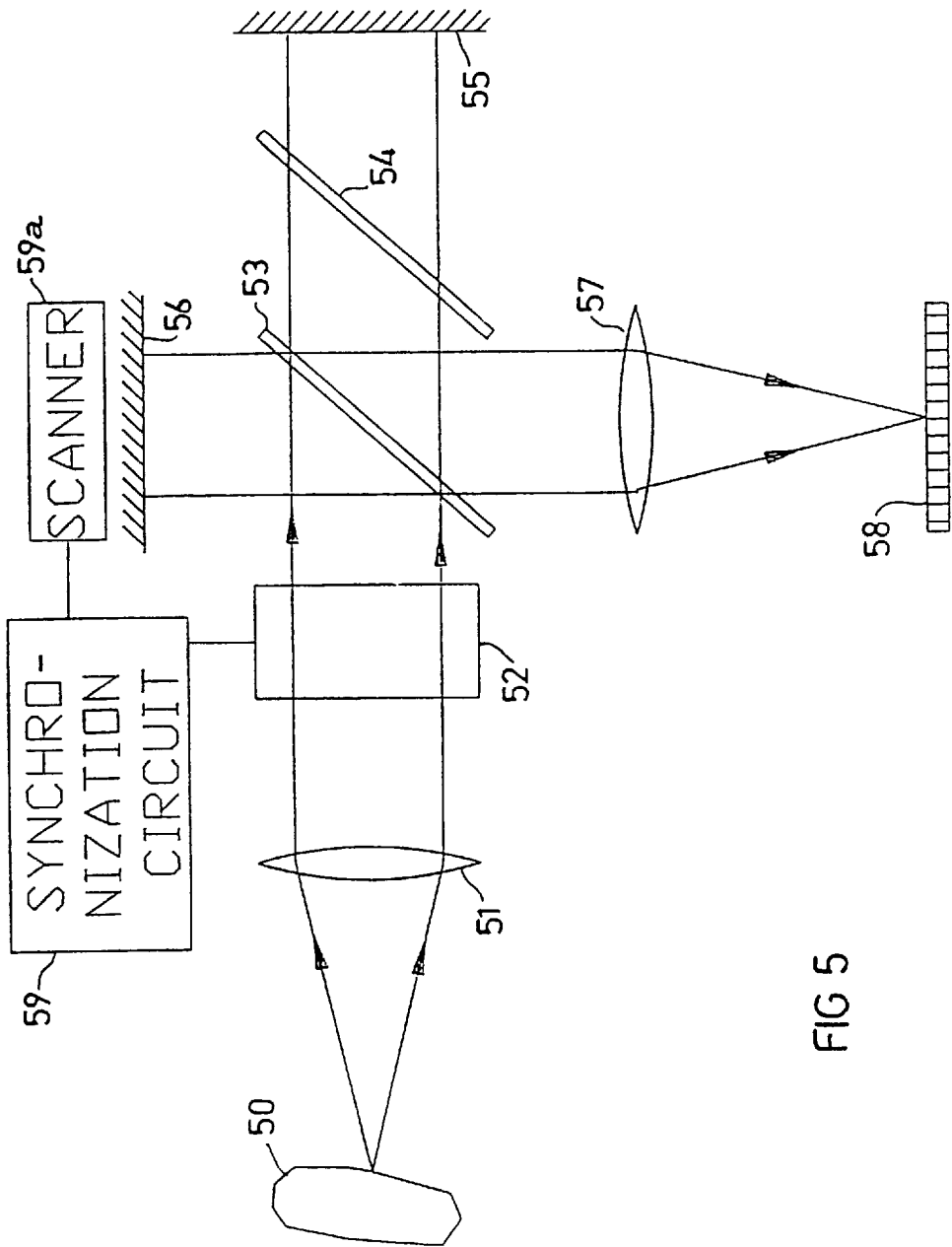
FIG. 5 is a diagram illustrating another moving-type interferometer, namely a Michelson type interferometer, which may be used as the interferometer in the imaging spectrometer of FIG. 4.

FIG. 5 illustrates an imaging spectrometer including a Michelson interferometer but of the moving type, similar to that of FIG. 3, namely wherein the OPD varies with moving an element of the interferometer. In the spectrometer of FIG. 5, the light from source 50 is collected by the optical collection system 51 and is collimated onto a scanning mirror 52 before being passed through the beam splitter 53 which splits the beam into the two arms. One arm includes a compensator 54 and a mirror 55, and the second arm includes merely a mirror 56. The light from the two mirrors is passed via beam splitter 53 and a focusing lens 57 onto an array of detectors 58.

In the spectrometer illustrated in FIG. 5, the scanning mirror is controlled by a synchronization circuit 59. This circuit also controls, via a scanner 59a, the distance between mirror 56 and beam splitter 53 with respect to mirror 55 and beam splitter 53, to thereby vary the OPD of the two arms.

The compensator 54 ensures that the central beam has an OPD equal to zero, so that the OPD, as seen by the different detectors of the array 58, is varied with the variation in the movement of mirror 56.

THE CONSTRUCTION OF FIG. 6

Figure 6:
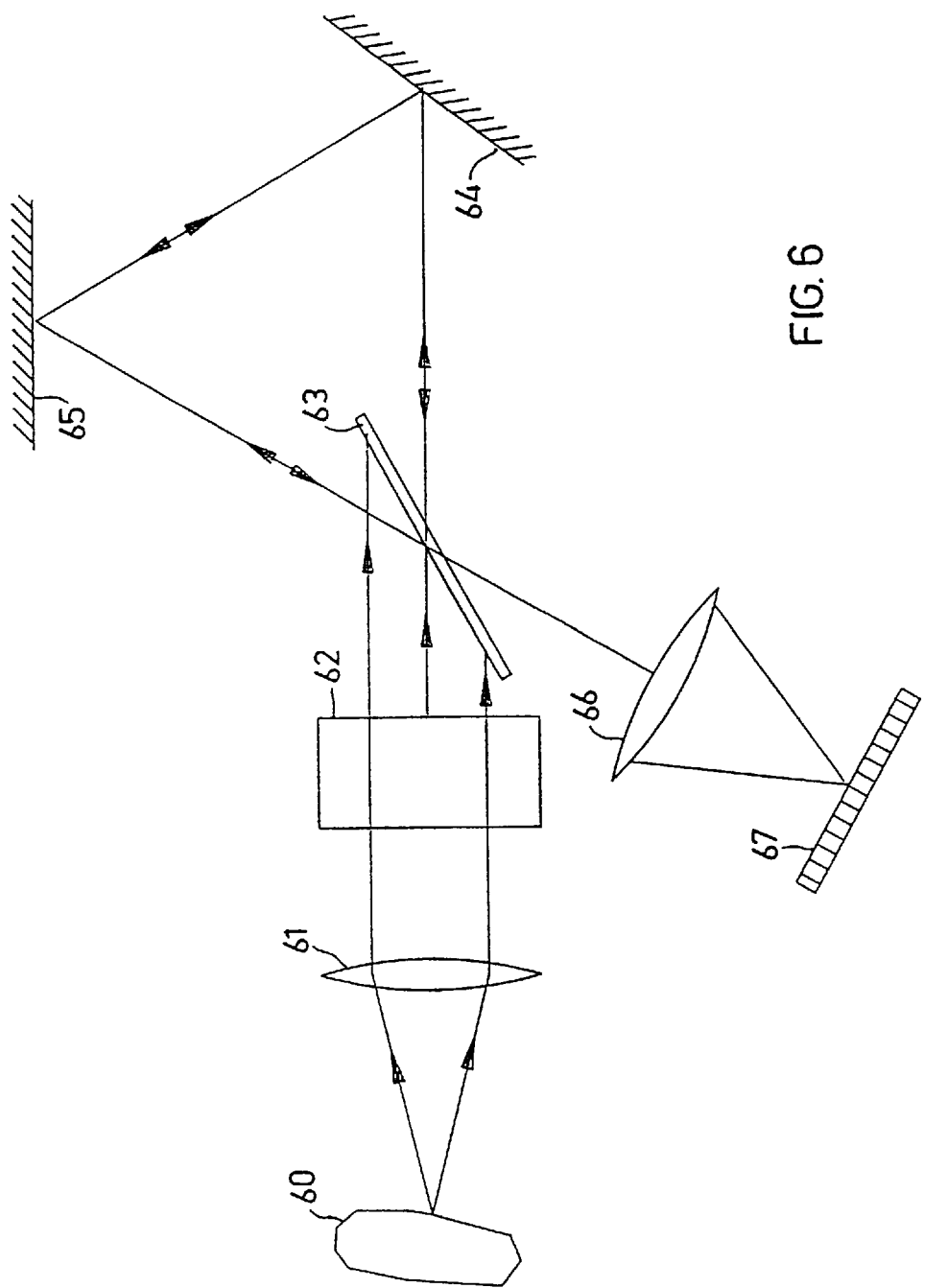
FIG. 6 illustrates another non-moving type interferometer, namely a modified Sagnac interferometer, as used in an imaging spectrometer in accordance with the invention.

FIG. 6 illustrates an imaging spectrometer constructed in accordance with the invention but utilizing another type interferometer, namely a modified Sagnac, of the non-moving type in that the OPD varies with the angle of incidence of the incoming radiation. As described above with respect to the imaging spectrometer illustrated in FIG. 4, a beam entering the interferometer at a small angle to the optical axis undergoes an OPD which varies linearly with this angle.

The modified Sagnac interferometer illustrated in the spectrometer of FIG. 6 is that described in E. Hecht, Optics, Addison-Wesley Publishing Company, p. 359 (1987). In this interferometer, all the spectral information from source 60 in all the pixels, after being collimated by the optical collection system 61, is scanned by a mechanical scanner 62. The light is then passed through a beam splitter 63 to a first reflector 64 and then to a second reflector 65, which reflects the light back through the beam splitter 63 and then through a focusing lens 66 to an array of detectors 67. This beam interferes with the one which is reflected by 63, then by 65, and finally by reflector 64. With a one-dimensional array, a two-dimensional scan is required; and with a two-dimensional array, only a one-dimensional scan is required.

At the end of one scan, every pixel has been measured through all the OPDs by different detectors at different times. Thus, a beam parallel to the optical axis is compensated, and a beam at an angle (φ) to the optical axis undergoes an OPD which is a function of the thickness of the beam splitter 63, its index of refraction, and the angle φ. The OPD is proportional to φ for small angles. By applying the appropriate inversion, and by careful bookkeeping, the spectrum of every pixel is calculated.

It will thus be seen that in this type of imaging spectrometer: i) the interferometer is in the region of the collimated beam, so the resolution is only limited by the number of detectors and not by the divergence of the radiation; ii) the beam splitter thickness and index of refraction are matched to the required resolution.

THE CONSTRUCTION OF FIG. 7

Figure 7:
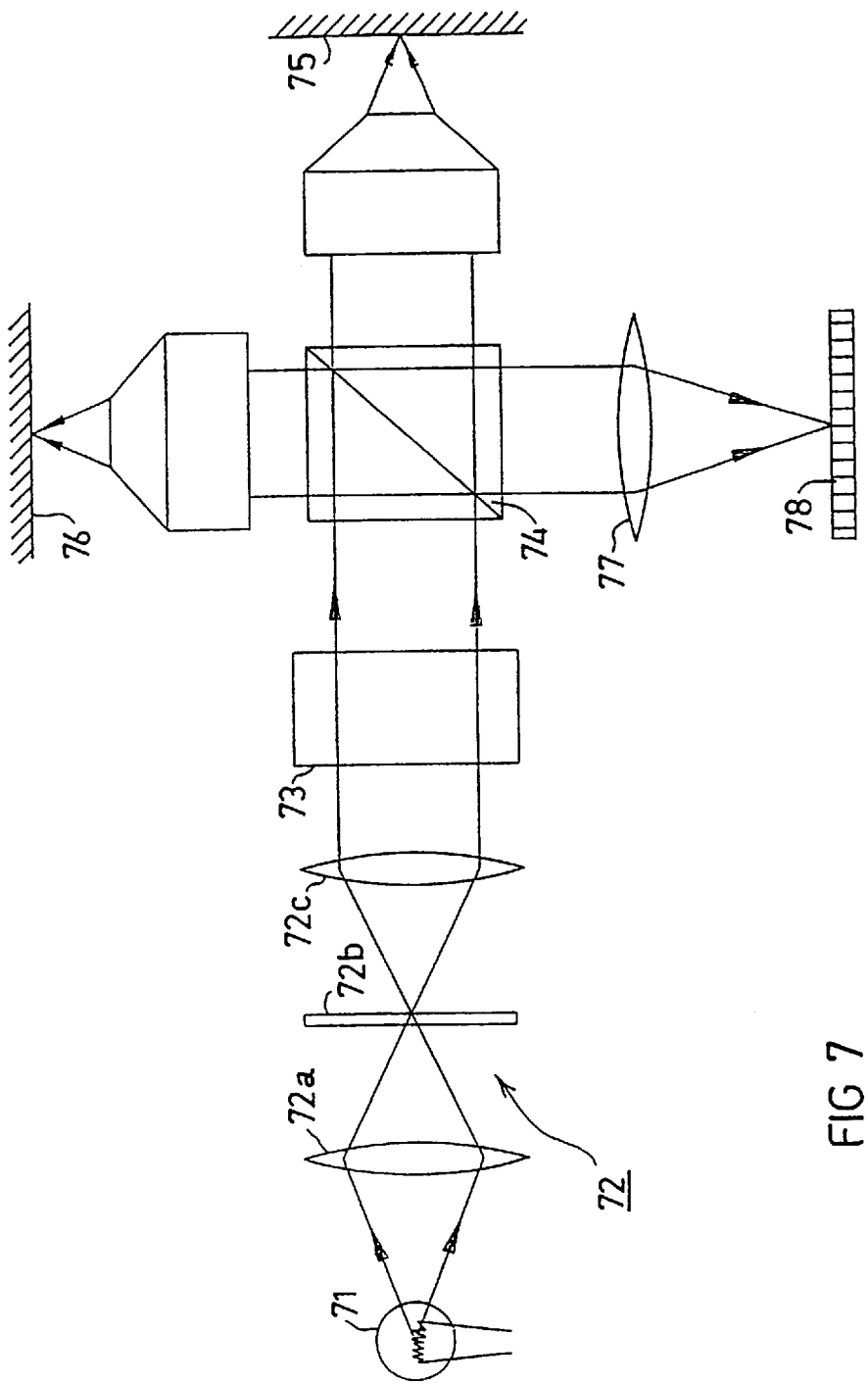
FIG. 7 illustrates the invention as embodied in a modified Michelson imaging spectrometer, as an example of another non-moving type interferometer, with focusing on the mirrors through microscope objectives.

FIG. 7 illustrates a further imaging spectrometer including a Michelson interferometer of the moving type, similar to that illustrated in FIG. 5, but used for focusing on the reflectors through microscope objectives. Thus, the spectrometer illustrated in FIG. 7 includes a light source 71 and a microscope optical system 72 including a condenser lens 72a, for focusing on the object 72b. Optical system 72 further includes a collimator lens 72c for directing the light through a scanner 73, through a beam splitter 74 to the two reflectors 75, 76, and then through a focusing lens 77 onto a detector array 78. The detector array 78 in the FIG. 7 configuration, as well as in the previously-described configurations, may be a CCD (charge coupled device).

The scanner 73 scans the field of view. Reflector 75, with the microscope system, move together along the optical axis to provide scanning of the OPD in synchronization with the scanner 73, as described above with respect to FIG. 5.

It will thus be seen that imaging spectrometers constructed in accordance with the present invention do not merely measure the intensity of light coming from every pixel in the field of view, but also measure the spectrum of each pixel in a predefined wavelength range. They thus better utilize all the radiation emitted by each pixel in the field of view at any given time, and therefore permit a significant decrease in the frame time and/or a significant increase in the sensitivity of the spectrometer. Such imaging spectrometers may include other types of interferometers and optical collection and focusing systems, and may be used in a wide variety of applications, including medical diagnostic applications, remote sensing for geological and agricultural investigations, and the like.

What is claimed is:

1. A method for simultaneously measuring the spectral intensity as a function of wavelength of all the pixels of a two-dimensional scene while detecting a real and stationary image of the scene, the method comprising the steps of:

(a) collecting incident light simultaneously from all points of the two-dimensional scene using collimating optics;

(b) passing at least a portion of said incident collimated light through an interferometer system having a number of elements, so that said light is first split into a plurality of coherent beams which travel along different optical paths inside said interferometer and then said plurality of coherent beams recombine to interfere with each other to form an exiting light, said interferometer system including an interferometer selected from the group consisting of low-finesse Fabry-Perot interferometers and interferometers wherein said light is split into a finite number of said coherent beams;

(c) passing said exiting light through a focusing optical system which focuses said exiting light on a detector having an array of detector elements;

(d) translating at least one of said elements of said interferometer system, so that an instantaneous optical path difference between said plurality of coherent beams generated by said interferometer system is scanned simultaneously for all the pixels of the scene wherefrom said portion of said collimated light originates, so that during said translating of said at least one element each of said detector elements receives the image of one and only one pixel of the scene, so that at least a portion of the real image of the scene is stationary on the detector array at any time during said translating the image is still visible and recognizable, and so that each of said detector elements produces a signal which is a particular linear combination of light intensity emitted by said pixel at different wavelengths, wherein said linear combination is a function of said instantaneous optical path difference; and (e) recording said signals of each of said detector elements as functions of time using a recording device.

2. The method of claim 1, wherein substantially all of said incident collimated light is passed through said interferometer system, and wherein said array of detector elements is two dimensional, so that said instantaneous optical path difference is scanned simultaneously for substantially all the pixels of the scene, so that each of said detector elements receives the image of one and only one pixel of the scene for the entire duration of the measurement, and so that substantially the entire real image of the scene is stationary on the detector array at any time during the measurement the image is still visible and recognizable.

3. The method of claim 1, wherein said array of detector elements is one dimensional, the method further comprising the step of:

(f) scanning said collimated light, so that only a substantially one-dimensional portion of said collimated light is passed through said interferometer system at one time.

4. The method of claim 1, wherein said incident light, prior to entering said interferometer system, is passed through an afocal telescope which simultaneously collects and collimates said light for each of the pixels of the scene.

5. The method of claim 1, wherein said incident light, prior to entering said interferometer system, is passed through a microscope which simultaneously collects and collimates said light for each of the pixels of the scene.

6. The method of claim 1, further comprising additional electronic means, automatically and simultaneously transferring all data in real time from all said elements of said detector array to a computer for display of a scene image on a screen for the purposes of focusing, tracking and monitoring the scene, recording intensities of said detector elements as a function of said optical path difference, and computing spectra of all the pixels.

7. The method of claim 1, wherein said interferometer is a low-finesse Fabry-Perot interferometer.

8. The method of claim 1, wherein said interferometer is of the type wherein said light is split into a finite number of said coherent beams.

9. The method of claim 8, wherein said interferometer is a Michelson interferometer.

10. A method for simultaneously measuring the spectral intensity as a function of wavelength of all the pixels of a two-dimensional scene located at infinity while detecting a real and stationary image of the scene, the method comprising the steps of:

(a) collecting naturally collimated incident light simultaneously from all points of the two-dimensional scene;

(b) passing said incident naturally collimated light through an interferometer system having a number of elements, so that said light is first split into a plurality of coherent beams which travel along different optical paths inside said interferometer and then said plurality of coherent beams recombine to interfere with each other to form an exiting light, said interferometer system including an interferometer selected from the group consisting of low-finesse Fabry-Perot interferometers and interferometers wherein said light is split into a finite number of said coherent beams;

(c) passing said exiting light through a focusing optical system which focuses said exiting light on a detector having an array of detector elements;

(d) translating at least one of said elements of said interferometer system, so that an instantaneous optical path difference between said plurality of coherent beams generated by said interferometer system is scanned simultaneously for all the pixels of the scene, so that during said translating of said at least one element each of said detector elements receives the image of one and only one pixel of the scene, so that at least a portion of the real image of the scene is stationary on the detector array at any time during said translating the image is still visible and recognizable, and so that each of said detector elements produces a signal which is a particular linear combination of light intensity emitted by said pixel at different wavelengths, wherein said linear combination is a function of said instantaneous optical path difference; and (e) recording said signals of each of said detector elements as functions of time using a recording device.

11. The method of claim 10, wherein said array of detector elements is two dimensional, so that each of said detector elements receives the image of one and only one pixel of the scene for the entire duration of the measurement, and so that substantially the entire real image of the scene is stationary on the detector array at any time during the measurement the image is still visible and recognizable.

12. The method of claim 10, wherein said array of detector elements is one dimensional, the method further comprising the step of:
(f) scanning said collimated light, so that only a substantially one-dimensional portion of said collimated light is passed through said interferometer system at one time.

13. The method of claim 10, wherein said interferometer is a low-finesse Fabry-Perot interferometer.

14. The method of claim 10, wherein said interferometer is of the type wherein said light is split into a finite number of said coherent beams.

15. The method of claim 14, wherein said interferometer is a Michelson interferometer.

16. A spectroscopic imaging device for simultaneously measuring the spectral intensity as a function of wavelength of all the pixels of a two-dimensional scene while detecting a real and stationary image of the scene, the device comprising:
(a) collimation means for directing light from the pixels of the scene towards an interferometer, said interferometer being selected from the group consisting of low-finesse Fabry-Perot interferometers and interferometers wherein incoming light is split into a finite number of coherent beams which travel along different optical paths, said interferometer having at least one moveable element which can be positioned to produce a multi-plexed spectral output of said light passing through said interferometer at a plurality of select positions of said moveable element;
(b) means operatively connected to the interferometer for positioning said moveable element of said interferometer, wherein said interferometer maintains the image fidelity of the scene as said light passes through said interferometer; and
(c) means for collimating and directing said light passing through said interferometer at a focal plane array detector comprising an array of charge coupled devices, wherein said charge coupled devices of said focal plane array detector measures the intensity of said light from at least some of the pixels of the scene at each of said plurality of select positions of said moveable element.

17. The device of claim 16, wherein said array of charge coupled devices is two dimensional and measures the intensity of said light from each of the pixels of the scene at each of said plurality of select positions of said moveable element.

18. The device of claim 16, wherein said array of charge coupled devices is one dimensional, the device further comprising:
(d) means for scanning said light directed towards said interferometer, so that only a substantially one dimensional portion of said light from the pixels of the scene is directed towards said interferometer at one time.

19. The device of claim 16, wherein the interferometer is a low-finesse Fabry-Perot interferometer.

20. The device of claim 16, wherein the interferometer is of the type wherein incoming light is split into a finite number of coherent beams which travel along different optical paths.

21. The device of claim 20, wherein the interferometer is a Michelson interferometer.

22. The device of claim 16, wherein each of said charge coupled devices produces a signal which is a particular linear combination of light intensity emitted by one of the pixels at different wavelengths, the device further comprising:
(d) a recording mechanism for receiving said signals of each of said charge coupled devices as functions of time using a recording device.

23. The device of claim 16, further comprising:
(d) means for converting said intensity of said light from optical retardation to wavelength.

24. The device of claim 16, further comprising:
(d) means for displaying an image of the scene derived from said intensity of said light at at least one wavelength.

25. The device of claim 16, further comprising:
(d) means for determining the position of said moveable element of said interferometer.

26. The device of claim 25, wherein said means for determining the position triggers said focal plane array detector to obtain an image of the scene at each of said select positions.

27. The device of claim 16, wherein said moveable element of said interferometer is a continuously moveable element.

28. The device of claim 16, wherein said moveable element is a mirror.

29. An apparatus for simultaneously measuring the spectral intensity as a function of wavelength of all the pixels of a two-dimensional scene while detecting a real and stationary image of the scene, the apparatus comprising:
(a) an interferometer system for receiving collected incident collimated light simultaneously from at least a portion of the two-dimensional scene, said light being first split into a plurality of coherent beams which travel in different directions inside said interferometer and then said plurality of coherent beams recombine to interfere with each other to form an exiting light, said interferometer system being translatable so that an optical path difference between said plurality of coherent beams generated by said interferometer is scanned simultaneously for all the pixels of the scene wherefrom said portion of said collimated light originates, said interferometer system including an interferometer selected from the group consisting of low-finesse Fabry-Perot interferometers and interferometers wherein said light is split into a finite number of said coherent beams;
(b) a focusing optical system through which said exiting light is passed to form a focused light;
(c) a detector having an array of detector elements on which said focused light is directed, so that at each instant each of said detector elements receives the image of one and only one pixel of the scene, so that at least a portion of the real image of the scene is stationary on the detector array and so that each of said detector elements produces a signal which is a particular linear combination of light intensity emitted by said pixel at different wavelengths, wherein said linear combination is a function of the instantaneous optical path difference; and
(d) a recording mechanism for receiving said signals of each of said detector elements as functions of time using a recording device.

30. The apparatus of claim 29, wherein said collimated light is received simultaneously from substantially all points of the two-dimensional scene, and wherein said array of detector elements is two dimensional, so that said optical path difference is scanned simultaneously for substantially all the pixels of the scene, so that each of said detector elements receives the image of one and only one pixel of the scene for the entire duration of the measurement, and so that substantially the entire real image of the scene is stationary on the plane of the detector array.

31. The apparatus of claim 29, wherein said array of detector elements is one dimensional, the apparatus further comprising:

(e) a mechanism for scanning said collimated light so that only a substantially one dimensional portion of said collimated light is passed through said interferometer system at one time.

32. The method of claim 29, wherein said interferometer is a low-finesse Fabry-Perot interferometer.

33. The method of claim 29, wherein said interferometer is of the type wherein said light is split into a finite number of said coherent beams.

34. The method of claim 33, wherein said interferometer is a Michelson interferometer.

* * * * *